United States Patent [19]

Zehner et al.

[11] 4,112,245

[45] Sep. 5, 1978

[54] PROCESS FOR THE PREPARATION OF ETHYLENE GLYCOL

[75] Inventors: Lee R. Zehner, Media, Pa.; R. Warren Lenton, Sewell, N.J.

[73] Assignee: Atlantic Richfield Company, Los Angeles, Calif.

[21] Appl. No.: 715,747

[22] Filed: Aug. 18, 1976

[51] Int. Cl.² ................... C07C 29/00; C07C 31/20
[52] U.S. Cl. ................................................. 568/864
[58] Field of Search ................................. 260/635 D

[56] References Cited

U.S. PATENT DOCUMENTS

| | | | |
|---|---|---|---|
| 2,060,880 | 11/1936 | Lazier | 260/635 D |
| 2,091,800 | 8/1937 | Adkins et al. | 260/635 D X |

FOREIGN PATENT DOCUMENTS 575,380   2/1946   United Kingdom.

OTHER PUBLICATIONS

Adams et al., Organic Reactions, vol. VIII, (1954), pp. 1–27.

*Primary Examiner*—Bernard Helfin
*Attorney, Agent, or Firm*—Delbert E. McCaslin

[57] ABSTRACT

A process for the preparation of ethylene glycol by the vapor phase hydrogenation of oxalate esters, such as a dibutyl oxalate, at elevated temperatures and at relatively low hydrogen pressures in the presence of a suitable hydrogenation catalyst, such as a copper chromite catalyst, while minimizing the hydrogenolysis of the glycol and other side reactions and maximizing the hydrogenation catalyst activity.

13 Claims, No Drawings

PROCESS FOR THE PREPARATION OF ETHYLENE GLYCOL

BACKGROUND OF THE INVENTION

In a co-pending application of Lee R. Zehner, Ser. No. 658,833, filed May 13, 1976, entitled PROCESS FOR THE PREPARATION OF OXALATE ESTERS and incorporated herein by reference, there is disclosed a process for the oxidative carbonylation of an alcohol with oxygen and carbon monoxide in the presence of a specific catalyst system to prepare oxalate esters. While oxalate esters find commercial application as solvents and as dye intermediates and the preparation of pharmaceuticals, there is nothing in the literature describing the vapor phase conversion of oxalate esters to produce the commercially valuable ethylene glycol.

The present invention is directed to an effective method for the vapor phase hydrogenation of oxalate esters to produce ethylene glycol. More particularly, the present process relates to the synthesis of ethylene glycol by hydrogenating oxalate esters at elevated temperatures and at relatively low hydrogen pressures in the presence of a hydrogenation catalyst such as a copper zinc chromite catalyst, a copper/alumina catalyst and other mixed copper and metal oxide hydrogenation catalysts, supported or unsupported, and mixtures thereof and useful as suitable catalysts for the hydrogenation in the vapor phase of an oxalate ester to produce ethylene glycol in high yield.

A number of prior art processes have been proposed for the preparation of alcohols and glycols by hydrogenation of certain esters of monobasic and higher dibasic acids in liquid phase and esters of hydroxy acetic acid in vapor phase reaction systems.

An article by H. Adkins, in R. Adams et al, ed., Organic Reactions, Vol. VIII, Chapter 1, John Wiley and Sons, Inc., New York, 1954, pp. 1–27, sets forth a general mechanism for the liquid phase hydrogenation of esters to alcohols in which it is mentioned that in the liquid phase, diethyl oxalate gives a good yield of ethylene glycol but only with a pressure much higher than normal liquid phase hydrogen pressures, i.e., higher than 4000 psi.

U.S. Pat. No. 2,305,104 discloses a process for the vapor phase hydrogenation of alkyl esters of hydroxy acetic acid utilizing a dual catalyst charged reaction zone at temperatures between 150° C. and 300° C. and pressures from 10 to 1000 atmospheres or higher.

British Pat. Nos. 555,240 and 575,380 disclose processes for the vapor phase catalytic hydrogenation of hydroxy acetic acid and its derivatives (esters) and an ester of glycollic acid respectively at temperatures ranging from 150° C. to 300° C. and pressures of from 10 to 1000 atmospheres to produce ethylene glycol.

Ethylene glycol is a valuable commercial chemical and finds application in deicing fluids, antifreeze, hydraulic fluids, manufacture of alkyd resins, solvents and polyester fibers.

SUMMARY OF THE INVENTION

This invention relates to a process for the preparation of ethylene glycol by the catalytic vapor phase hydrogenation of oxalate esters especially the dialkyl oxalates such as dimethyl, diethyl, dipropyl and dibutyl oxalates, by passing the oxalate ester together with hydrogen at elevated temperatures and relatively low hydrogen pressures and at a desired space velocity over a suitable hydrogenation catalyst in a suitable pressure reactor. By utilizing an oxalate feed which has been essentially desulfurized and within the operating conditions of the invention, side reactions are minimized and the activity of the hydrogenation catalysts greatly increased since sulfur contamination even in very small amounts causes a rapid loss of catalyst activity and low yield of ethylene glycol.

It is a primary object of this invention to provide a process for the preparation of ethylene glycol in high yield and high conversion of reactants, by the catalytic hydrogenation of an oxalate ester.

It is another object of this invention to provide a process wherein oxalate esters essentially free of sulfur are hydrogenated to ethylene glycol in the vapor phase, and temperatures and pressures of hydrogenation controlled to maximize hydrogenation catalyst activity and yield.

A further object is to provide novel optimum operating conditions for the catalytic vapor phase hydrogenation of an oxalate ester to ethylene glycol.

These and other objects and advantages of this invention will become apparent from the description of the invention which follows and from the claims.

DESCRIPTION OF THE INVENTION

In accordance with the invention, ethylene glycol is prepared from an oxalate ester, such as diethyl oxalate, by subjecting an essentially sulfur free oxalate ester to catalytic vapor phase hydrogenation at elevated temperatures and relatively low hydrogen pressures to produce the ethylene glycol along with the corresponding alcohol.

A general postulated equation for the reaction may be represented as follows:

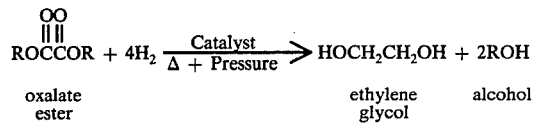

$$\underset{\text{oxalate ester}}{\text{ROCCOR}} + 4H_2 \xrightarrow{\text{Catalyst}}_{\Delta + \text{Pressure}} \underset{\text{ethylene glycol}}{\text{HOCH}_2\text{CH}_2\text{OH}} + \underset{\text{alcohol}}{2\text{ROH}}$$

wherein R is a substituted or unsubstituted alkyl or aralkyl group which may contain other substituents such as alkoxy, amino, carboxy, cyano, etc. radicals which in general do not interfere with the reaction of the invention. The alcohol coproduced with the desired ethylene glycol by the hydrogenation of the oxalate ester may be readily separated from the reaction mixture and converted back to an oxalate ester by the oxidative carbonylation reaction as, for example, by the process as set forth in the aforementioned Lee R. Zehner application.

The catalytic vapor phase hydrogenation process of the invention may, for example, be carried out in any suitable reactor such as a tube reactor, wherein an oxalate ester heated to the vaporous or gaseous state, to be hydrogenated, together with hydrogen, at the desired pressures and temperatures are passed over a hydrogenation catalyst which may be in the form of a fixed, fluidized or moving catalyst bed. Since vapor phase hydrogenation reactions are generally exothermic cooling means may be employed interior and/or exterior of the reactor to control and maintain the temperature within the desired reaction temperature range. The vaporous reaction products from the hydrogenation reactor may be recovered and treated by any conventional method such as by condensation and subsequent fractional distillation, to effect separation of the ethylene glycol and alcohol from any unreacted materials and and by-products. The reaction is generally carried out in a cyclical or continuous manner and a suitable recycle of any excess or unreacted hydrogen or oxalate ester may be employed.

The oxalate esters which may be employed in the process of the invention conform to the general formula

wherein R is as hereinabove described. The preferred esters for use in the hydrogenation process for the preparation of ethylene glycol are those esters wherein R is an alkyl group containing from 1 to 8 carbon atoms such as dimethyl oxalate, diethyl oxalate, dibutyl oxalates, diamyl oxalates, etc. The esters are preheated and vaporized, as may be determined by their vapor pressure, to insure that essentially all of the ester is in the vapor state when passed, along with hydrogen, over the catalyst bed. The catalyst bed is maintained at a temperature high enough to prevent condensation of the oxalate ester or the product ethylene glycol. The temperature and pressure of the reaction are such that the reaction products issuing from the reaction zone are in the vapor phase.

In the hydrogenation of the oxalate ester, the hydrogen is generally employed in an excess of the stoichiometric amount required to convert the oxalate ester to ethylene glycol and the corresponding alcohol. Thus, the preferred molar ratio of hydrogen to oxalate ester entering the reaction zone is 30:1. Higher or lower ratios of hydrogen to oxalate ester may be employed in the process provided the ester is in the vapor state and the hydrogen is employed in at least the stoichiometric amount of 4:1.

The hydrogenation catalysts which may be employed in the process of this invention have been described in the prior art and any known hydrogenation catalyst, or mixture of catalysts, useful for the conversion of esters to alcohols may be employed. Catalysts and the preparation thereof, such as are described in U.S. Pat. Nos. 2,094,611, 2,305,104 and 3,374,184 may be used. In general, hydrogenation catalysts containing copper either in the elementary form or combined with oxygen, as well as other hydrogenating metal oxides employed in conjunction with copper, supported or unsupported, may be used. Especially preferred catalysts are the copper zinc chromite or copper chromite catalysts which may be promoted with barium or sodium hydroxide and which have been reduced in hydrogen.

Representative hydrogenation catalysts suitable for use in this invention include, for example, in addition to those above noted, zinc/copper/cadmium/chromite catalyst, copper ammonium chromate, zinc chromium oxide, Raney nickel, nickel on kieselguhr and chromites of manganese and magnesium. Other suitable catalysts comprise compositions of tin, silver, cadmium, zinc or lead and oxides of chromium of these metals. Many suitable hydrogenation catalysts are commercially available such as the copper zinc chromite catalyst (Girdler T-359), copper barium chromite (Harshaw Cu 1107) catalysts and the sodium hydroxide-promoted copper chromite (Houdry 536 CP) catalyst.

The hydrogenation catalysts may be prepared by any convenient method such as by precipitation or fusion. The preferred copper chromite and copper zinc chromite catalysts are precipitated catalysts and may be prepared by the method set forth in the above disclosed British Pat. No. 575,380 and then reduced in hydrogen. A copper chromite hydrogenation catalyst may also be prepared, for example, by neutralizing 1 mole of chromium trioxide and 1 mole of copper (II) nitrate trihydrate in aqueous ammonium carbonate to a pH of 7. The precipitate is washed and dried and then calcined at 400° C. The calcined catalyst is then sized to a suitable 8-14 or 8-30 mesh and reduced in hydrogen at, for example, 200° C. for 17 hours.

The vapor phase hydrogenation catalysts employed in the process of this invention may be subject to a rapid loss of catalyst activity or degradation due to various factors and conditions which must be reduced, controlled or eliminated to make the process economical. In such reactions, catalyst poisoning and the resulting loss in catalyst activity appears to be due to uncontrolled or improper dispersion of the exothermic heat of reaction causing hydrogenolysis of product ethylene glycol and other factors of a chemical nature, e.g., in the hydrogenation of diethyl oxalate, the formation of copper salts (oxalates and glycolates), 2-ethoxyethanol, ethyl glycolate, as well as the formation of polymeric esters, e.g., polyglycolates or polymeric ethylene oxalate, which when deposited on the catalyst surface reduces the hydrogenation activity thereof. Oxalate esters per se do not polymerize in either the preheater, the reactor or on the surface of the catalyst. Other factors include catalyst poisons, such as sulfur or halogen compounds, which may contact the catalyst with the feed hydrogen or with the feed oxalate ester to be hydrogenated, such as hydrogen sulfide and organic sulfates, or a combination of the above, these, or other causes. In general, the amount of by-products formed in the reaction is indicative of catalyst degradation.

By the process of the present invention hydrogenolysis including the attendant problem of by-product formation on the catalyst surface, as well as poisoning and degradation of and loss of catalyst activity from the feed materials is substantially minimized. The hydrogenation catalyst activity may be substantially maximized by a number of variables, namely, (1) prereduction of the hydrogenation catalysts especially the copper-containing catalysts, to reduce or obviate the oxalate ion poisoning, as well as to increase the hydrogenation activity of the catalyst, (2) removal of sulfur from the feed oxalate ester to preferably less than 0.4 ppm sulfur, (3) the use of an essentially sulfur and halogen free hydrogen, (4) use of a catalyst bed diluted or mixed with inert support materials such as tabular alumina, silica, glass beads, etc., and thereby increase the dispersion of the exothermic heat of reaction reducing or eliminating hot spots in the bed and thus decrease the extent of hydrogenolysis, and (5) if necessary, a purge of the reaction catalyst system periodically with hydrogen during a shutdown to decompose contaminants, especially copper (II) oxalate, which may have accumulated on the catalyst surface. The hydrogen purge may be carried out at reaction temperatures (catalyst bed temperatures) and reaction pressures and generally for periods of from 5 to 20 hours.

Prereduction of the hydrogenation catalysts such as copper chromite or copper zinc chromite catalysts is carried out to essentially reduce the copper compounds, e.g., copper oxide, to the copper metal. Such reduction is most conveniently accomplished with hydrogen in suitable apparatus. Actual reduction procedures are well known in the art and they may vary depending on the catalyst. Hydrogen reductions are generally carried out at a temperature of from 100° C. to 450° C. with hydrogen pressures of 0.01 to 10 atmospheres. Any copper oxides which may be formed in the reaction are quickly reduced to metallic copper in the presence of reactant hydrogen.

Sulfur, usually in the form of an organic sulfate, i.e., ethyl hydrogen sulfate, diethyl sulfate and di-n-butyl sulfate, etc., may be present for example, as a contaminant in the corresponding dialkyl oxalate ester to be hydrogenated. Since such sulfur which may be present in the oxalate in amounts as high as 700 ppm, will rapidly poison the hydrogenation catalyst, especially copper chromite, it must be removed from the feed oxalate to a low level and preferably to amounts of less than 0.4 ppm. A convenient method, for example, for reducing the sulfur content of diethyl oxalate is to treat the oxalate ester with sodium ethoxide (sodium ethylate) at a temperature of 80° C. with, if necessary, subsequent neutralization of any unreacted sodium ethoxide with acetic acid and distillation of the oxalate solution leaving behind the resulting non-volatile sodium sulfate. In order to avoid the possible problem of having mixed esters and other side reactions, sodium methylate and sodium butylate, for example, are used to treat the respective dialkyl oxalate in the same manner.

Hydrogen sulfide and/or hydrogen chloride, which may be a contaminant in the hydrogen feed gas and which may cause catalyst poisoning, may be removed or substantially reduced by any conventional gas scrubber system. Convenient methods are to pass the gas through a bed of a mixture of $Fe_2O_3$ and fly ash, or through a bed of $CuO/ZnO$.

In general, the process of the present invention is carried out by passing an essentially sulfur free vaporized oxalate ester, together with essentially sulfur free hydrogen over a suitable prereduced hydrogenation catalyst maintained at a reaction (catalyst bed) temperature of between 150° C. and 300° C. and preferably between 200° C. and 230° C., at a hydrogen pressure of between 15 psia and 1000 psia and preferably between 150 psia and 475 psia and at a space velocity (the volumes of vaporous oxalate/hydrogen gaseous mixture calculated at ambient temperature and pressure passed over a unit volume of hydrogenation catalyst bed per hour) of between 3000 $hr^{-1}$ and 20,000 $hr^{-1}$ and preferably between 8000 $hr^{-1}$ and 15,000 $hr^{-}$. The liquid hourly space velocity of oxalate ester (calculated as the liquid volume of oxalate per unit volume of hydrogenation catalyst) passed over the catalyst in vaporous form and found to be suitable in the process of the invention is 0.001 $hr^{-1}$ to 5.0 $hr^{-1}$ and preferably 1.0 $hr^{-1}$ to 3.5 $hr^{-1}$.

The following examples are provided to illustrate the present invention in accordance with the principles of this invention but are not to be construed as limiting the invention in any way except as indicated by the appended claims.

In all the examples which follow the hydrogenation runs were carried out in a 1 inch inside diameter straight through tube reactor 3 feet in length and equipped with an external heating jacket to bring the catalyst bed to reaction temperature. A hydrogenation catalyst bed (100 ml) (with or without inert dilution) was positioned in the middle of the reactor tube and held with glass wool plugs. A metal spiral channel to distribute and circulate the vapors was positioned on top of the catalyst bed. A heated tube packed with glass beads to vaporize the oxalate ester and preheat the hydrogen prior to entry into the hydrogenation reactor was employed. The vaporous product and by-product effluent from the reactor were conducted into a straight through standard water cooled tube condenser and then into a liquid/gas separator. The reaction products were analyzed by gas-liquid chromatography (glc) and NMR spectral analysis for ethylene glycol, alcohol, unreacted oxalate ester, and by-products, etc. The desired ethylene glycol and corresponding alcohol may be subsequently separated from the condensate by fractional distillation.

EXAMPLE I

The hydrogenation reactor was charged with 100 ml. of a prereduced (213° C. with 1 atmosphere hydrogen) copper, zinc chromite catalyst (Girdler T-359) without inert dilution. Diethyl oxalate, containing 260 ppm sulfur, and hydrogen were preheated at 190° C. vaporizing the diethyl oxalate. The vaporized oxalate/hydrogen gaseous mixture was introduced into the reactor and over the catalyst at 215° C. under 1000 psia hydrogen pressure at a space velocity (SV) of approximately 4900 $hr^{-1}$ and a liquid hourly space velocity (LHSV) of 0.3 $hr^{-1}$. A reaction exotherm was noted. The reaction was run for a total of 9 hours and liquid samples collected continuously. Gas-liquid chromatographic analysis of the liquid product samples showed from 11.7 to 18.9 weight percent ethylene glycol, 44.5 to 62.7 weight percent ethanol and 6.4 to 30.9 weight percent unreacted diethyl oxalate along with from 9.7 to 22.6 weight percent of undetermined byproducts. Analysis of the catalyst showed the presence of 0.14 weight percent sulfur as compared to 0.09 weight percent sulfur on the unused catalyst, and the presence of copper oxalate.

EXAMPLE II

The procedure and conditions of Example I were repeated using a prereduced barium promoted copper chromite catalyst (Harshaw Cu 1107). The reaction was carried out for a total of 18 hours and liquid product samples collected continuously. Analysis of the liquid product samples collected showed from 5.0 to 12 weight percent ethylene glycol, 21 to 42 weight percent ethanol and 29.1 to 40.9 weight percent unreacted diethyl oxalate. Catalyst degradation was again caused by the sulfur content of the diethyl oxalate feed. The theoretical yield of ethylene glycol and the corresponding ethanol by the catalytic hydrogenation of diethyl oxalate using stoichiometric amounts of reactants is 40 weight percent and 60 weight percent respectively.

EXAMPLE III

The hydrogenation reactor was charged with 50 ml of a prereduced (225° C. with 70 liters per hour hydrogen at atmospheric pressure for 4.5 hours) sodium hydroxide-promoted copper chromite catalyst prepared according to Example IV of U.S. Pat. No. 3,374,184 (available commercially as Houdry 536 CP catalyst). The catalyst was mixed on a 50 ml/50 ml basis with 8-14 mesh tabular alumina. Diethyl oxalate which was desulfurized to a sulfur content of 17 ppm by reacting the oxalate with sodium ethoxide at 80° C. with subsequent neutralization of the unreacted ethoxide with acetic acid and distilling off the diethyl oxalate was preheated along with hydrogen at 200° C. and introduced into the reactor and over the catalyst at a temperature of 215° C. under 450 psia hydrogen pressure at a SV, based on the volume of 100 ml of catalyst bed, of 5000 hr$^{-1}$ and a LHSV of diethyl oxalate of 0.5 hr$^{-1}$. A reaction exotherm was noted which moved down the bed from the beginning of the run when the diethyl oxalate/hydrogen vapor mixture contacted the catalyst bed. Liquid samples were collected every 15 minutes and the reaction carried out for a 10 hour period at which time the catalyst activity decreased due to apparent sulfur poisoning. Gas-liquid chromatographic analysis of the samples showed yields of from 20 to 37.5 weight percent ethylene glycol, 30–64 weight percent ethanol and 100 percent conversion of diethyl oxalate. The catalyst diluted with inert alumina reduced the intensity of the exotherm and decreased the extent of hydrogenolysis.

EXAMPLE IV

The procedure of Example III was repeated using the same type catalyst which was prereduced at 200° C. under 1 atmosphere of hydrogen for 17 hours and the diethyl oxalate desulfurized with sodium ethoxide as in Example III to a sulfur content of less than 0.2 ppm. The feed hydrogen was passed through a sulfide scrubber containing a $Fe_2O_3$/fly ash mixture prior to preheating and mixing with the vaporized diethyl oxalate. Reaction conditions were catalyst bed temperature at 200° C., 450 psia hydrogen pressure, vapor space velocity of 3000 hr$^{-1}$ and a LHSV of from 0.2 to 0.5 hr$^{-1}$. The hydrogenation run was carried out for a period of 95 hours at which time the catalyst appeared stable as shown by a stable exotherm level at less than ⅓ of the catalyst bed length and continued high selectivity to ethylene glycol at 100 percent conversion of diethyl oxalate. Reaction product samples of the condensed liquid product were taken every 15 minutes and analyzed by glc analysis. Analysis of the samples showed from 36.2 to 40 weight percent ethylene glycol, water concentration of from 0.6 to 1.7 weight percent, 0 weight percent of diethyl oxalate (100 percent conversion of the diethyl oxalate) and trace amounts of ethyl glycolate and diethylene glycol.

EXAMPLE V

The hydrogen reactor was charged with 53 ml of a 8–14 mesh copper chromite catalyst, diluted with 50 ml of 8–14 mesh tabular alumina. The catalyst was prepared by neutralizing with a solution of ammonium carbonate, to a pH of 7, a solution of 1 mole of chromium trioxide and 1 mole of copper (II) nitrate trihydrate in 2 liters of water at room temperature. The precipitate was washed and dried and calcined at a temperature of 400° C., ground and sized to 8–14 mesh. The catalyst was then completely reduced under 1 atmosphere of hydrogen at 200° C. for 54 hours. Diethyl oxalate, desulfurized by treating with sodium ethoxide to a sulfur content of less than 0.4 ppm, and hydrogen were preheated at 200° C. to vaporize the diethyl oxalate. The vaporized diethyl oxalate/hydrogen mixture was introduced into the reactor and over the catalyst at 220° C. under 450 psia hydrogen pressure at a space velocity of 10,000 hr$^{-1}$ and a LHSV of 1.5 hr$^{-1}$. The reaction was run for a period of 460 hours with only a slight degradation of the catalyst being apparent. Formation of trace amounts of non-selective by-products, i.e., 2-ethoxyethanol, ethyl glycolate and diethyl ether was noted after 110 hours of catalyst use. Liquid samples of reaction product were collected every 30 minutes and analyzed by glc analysis. Analysis of the samples showed a 95+ percent selectivity to ethylene glycol with a 100 percent conversion of the diethyl oxalate with yields of from 36.8 to 39.6 weight percent ethylene glycol, 0.83 to 1.58 weight percent water, 0 weight percent unreacted diethyl oxalate and trace amounts of 2-ethoxyethanol, ethyl glycolate and diethyl ether.

EXAMPLE VI

The hydrogenation reactor was charged with 53 ml of 8–14 mesh copper chromite catalyst prepared as set forth in Example V and mixed with 50 ml of 8–14 mesh tabular alumina. Diethyl oxalate with a sulfur content of less than 0.2 ppm, and hydrogen, were preheated at 200° C. in order to vaporize the diethyl oxalate. The vaporous mixture of oxalate/hydrogen was introduced into the reactor and over the catalyst at 232° C. (catalyst bed temperature) under a 200 psia hydrogen pressure, a SV of 12,000 hr$^{-1}$ and LHSV of 1.8 hr$^{-1}$ and with a mole percent feed of diethyl oxalate of approximately 2.8 percent. The reaction was run for a period of 14 hours and liquid samples taken of the condensed reaction product every 15 minutes. Analysis of the liquid samples showed an average of 34 weight percent ethylene glycol, 52 weight percent ethanol, 3 weight percent water, 0 weight percent diethyl oxalate, and trace amounts of ethyl glycolate.

EXAMPLE VII

The reactor was charged with 53 ml of 8–14 mesh copper chromite catalyst prepared as set forth in Example V mixed with 50 ml of 8–14 mesh tabular $Al_2O_3$. Di-n-butyl oxalate with a sulfur content of less than 0.4 ppm and hydrogen were preheated at 200° C. and the vaporous mixture of oxalate/hydrogen introduced into the reactor and over the catalyst bed at a temperature of 230° C. under 450 psia hydrogen pressure, at SV of 12,000 hr$^{-1}$ and a LHSV of 2.0 hr$^{-1}$. During the reaction an exotherm was noted raising the temperature to approximately 255° C. The reaction was run for a 12 hour period and samples taken of the condensed liquid product every 15 minutes. Glc analysis of the collected samples showed from 24.6 to 27.3 weight percent ethylene glycol, 59.3 to 71.5 weight percent butanol, 0.95 to 1.76 weight percent water and trace amounts of ethanol and butyl glycolate with 100 percent conversion of the di-n-butyl oxalate.

EXAMPLE VIII

The procedure of Example VII was repeated using the same type of prereduced catalyst. Reaction conditions were catalyst bed temperature 230° C. at 200 psia hydrogen pressure, a SV of vapor of 12,000 hr$^{-1}$ with a LHSV of 0.3hr$^{-1}$ and a di-n-butyl oxalate concentration of 2.9 mole percent. An exotherm was noted. The hydrogenation run was carried out for a period of 18 hours and liquid samples taken every 15 minutes. Glc analysis of the reaction product samples showed from 22.5 to 26.2 weight percent ethylene glycol, 53 to 63.5 weight percent butanol, 1.35 to 1.81 weight percent water, 1.0 to 2 weight percent ethanol and 0 weight percent unreacted di-n-butyl oxalate. The theoretical yield of ethylene glycol and the corresponding butanol by the catalytic hydrogenation of di-n-butyl oxalate using stoichiometric amounts of reactants is 29.5 weight percent ethylene glycol and 70.5 weight percent butanol respectively.

EXAMPLE IX

The reactor was charged with the same amount and type prereduced diluted catalyst as set forth in Example V. Di-isobutyl oxalate having a sulfur content of less than 0.3 ppm and hydrogen were preheated at 200° C. The vaporous oxalate/hydrogen mixture was introduced into the reactor and over the catlyst at a catalyst reaction bed temperature of 220° C. under 200 psia hydrogen pressure, at a space velocity of 12,000 hr$^{-1}$ and a liquid hourly space velocity of 3.0 hr$^{-1}$. An exotherm was noted raising the temperature to 260° C. The reaction was run for a period of 25 hours and samples of the condensed liquid product taken every 15 minutes. Glc analysis of the collected samples showed from 23.9 to 27.8 weight percent ethylene glycol, 57.2 to 70.9 weight percent isobutanol, 0.90 to 1.65 weight percent water, trace amounts of ethanol and isobutyl glycolate with 100 percent conversion of the di-isobutyl oxalate.

EXAMPLE X

Using the same amount, and type of prereduced diluted catalyst as in Example IX a molten dimethyl oxalate and hydrogen were preheated at 200° C. The vapor mixture containing less than 0.2 ppm sulfur was introduced into the reactor and over the catalyst in vapor form at a temperature of 225° C. under 300 psia hydrogen pressure, a space velocity of 15,000 hr$^{-1}$ and a liquid hourly space velocity of 3.0 hr$^{-1}$. A reaction exotherm was noted. The reaction was run for 36 hours and samples of condensed liquid product collected every 15 minutes. Glc analysis of the samples showed 36.5 to 47.3 weight percent ethylene glycol, 35.3 to 46.1 weight percent methanol, 0.48 to 1.02 weight percent water, and a trace amount of ethanol and methyl glycolate with 100 percent conversion of the dimethyl oxalate.

We claim:

1. A process for the preparation of ethylene glycol which comprises reacting under vapor phase conditions a gaseous mixture of an oxalate ester having the formula

wherein R is an alkyl or aralkyl group which may contain substituents which would not interfere with the reaction, said oxalate ester having a sulfur content of less then 0.4 ppm, with an essentially sulfur-free hydrogen at a pressure of between about 15 psia and 1000 psia, the molar ratio of hydrogen to oxalate ester in the reaction being from 4:1 to 30:1, at a temperature in the range of about 150° C. and 300° C., and at a space velocity between about 3000 hr$^{-1}$ and 20,000 hr$^{-1}$ and a liquid hourly space velocity of between about 0.001 hr$^{-1}$ and 5.0 hr$^{-1}$ in the presence of an effective amount of a copper-containing hydrogenation catalyst which catalyst has been subjected to a prereduction in hydrogen at a temperature of from about 100° C. to 450° C. and at a hydrogen pressures of from about 0.01 to 10 atmospheres, and recovering the ethylene glycol.

2. A process according to claim 1 wherein the oxalate ester is selected from the group consisting of dimethyl oxalate, diethyl oxalate and dibutyl oxalates.

3. A process according to claim 1 wherein the reaction is carried out at a temperature in the range of about 200° C. to 230° C.

4. A process according to claim 1 wherein the reaction is carried out at a pressure of between about 150 psia and 475 psia.

5. A process according to claim 1 wherein the space velocity is between about 8000 hr$^{-1}$ and 15,000 hr$^{-1}$.

6. A process according to claim 1 wherein the liquid hourly space velocity is between 1.0 hr$^{-1}$ and 3.5 hr$^{-1}$.

7. A process according to claim 1 wherein the hydrogenation catalyst is selected from the group consisting of copper zinc chromite, copper chromite, copper barium chromite, and sodium hydroxide-promoted copper chromite catalysts.

8. A process according to claim 1 wherein the catalyst is diluted with an inert support material.

9. A process according to claim 8 wherein the inert support material is selected from the group consisting of alumina, silica and glass beads.

10. A process according to claim 1 wherein the hydrogenation catalyst is periodically purged with hydrogen at reaction conditions.

11. A process for the preparation of ethylene glycol which comprises reacting under vapor phase conditions a gaseous mixture of a diethyl oxalate having a sulfur content of less than 0.4 ppm, with an essentially sulfur-free hydrogen, at a molar ratio of hydrogen to diethyl oxalate of from 4:1 to 30:1 and which mixture is preheated in order to vaporize said oxalate, at a pressure of between about 150 psia and 475 psia, a temperature in the range of about 200° C. to 230° C., a space velocity between about 8000 hr$^{-1}$ and 15,000 hr$^{-1}$ and a liquid hourly space velocity of between about 1.0 hr$^{-1}$ and 3.5 hr$^{-1}$ in the presence of an effective amount of a hydrogenation catalyst selected from the group consisting of copper zinc chromite, copper chromite, copper barium chromite, and sodium hydroxide-promoted copper chromite catalysts said hydrogenation catalyst having been prereduced in hydrogen at a temperature of from about 100° C. to 450° C. and at hydrogen pressures of from about 0.01 to 10 atmospheres, and recovering the ethylene glycol.

12. A process for the preparation of ethylene glycol which comprises reacting under vapor phase conditions a gaseous mixture of a dibutyl oxalate having a sulfur content of less than 0.4 ppm, with an essentially sulfur-free hydrogen, at a molar ratio of hydrogen to dibutyl oxalate of from 4:1 to 30:1 and which mixture is preheated in order to vaporize said oxalate, at a pressure of between about 150 psia and 475 psia, a temperature in the range of about 200° C. to 230° C., a space velocity between about 8000 hr$^{-1}$ and 15,000 hr$^{-1}$ and a liquid hourly space velocity of between about 1.0 hr$^{-1}$ and 3.5 hr$^{-1}$ in the presence of an effective amount of a hydrogenation catalyst selected from the group consisting of copper zinc chromite, copper chromite, copper barium chromite, and sodium hydroxide-promoted copper chromite catalysts said hydrogenation catalyst having been prereduced in hydrogen at a temperature of from about 100° C. to 450° C. and at hydrogen pressures of from about 0.01 to 10 atmospheres, and recovering the ethylene glycol.

13. A process for the preparation of ethylene glycol which comprises reacting under vapor phase conditions a gaseous mixture of a dimethyl oxalate having a sulfur content of less than 0.4 ppm, with an essentially sulfur-free hydrogen, at a molar ratio of hydrogen to dimethyl oxalate of from 4:1 to 30:1 and which mixture is preheated in order to vaporize said oxalate, at a pressure of between about 150 psia and 475 psia, a temperature in the range of about 200° C. to 230° C., a space velocity between about 8000 hr$^{-1}$ and 15,000 hr$^{-1}$ and a liquid hourly space velocity of between about 1.0 hr$^{-1}$ and 3.5 hr$^{-1}$ in the presence of an effective amount of a hydrogenation catalyst selected from the group consisting of copper zinc chromite, copper chromite, copper barium chromite, and sodium hydroxide-promoted copper chromite catalysts said hydrogenation catalyst having been prereduced in hydrogen at a temperature of from about 100° C. to 450° C. and at hydrogen pressures of from about 0.01 to 10 atmospheres, and recovering the ethylene glycol.

* * * * *